(12) United States Patent
Wool

(10) Patent No.: US 10,946,178 B1
(45) Date of Patent: *Mar. 16, 2021

(54) METHOD FOR PREVENTING CONTRAST INDUCED NEPHROPATHY

(71) Applicant: Thomas J. Wool, Montgomery, AL (US)

(72) Inventor: Thomas J. Wool, Montgomery, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/913,083

(22) Filed: Jun. 26, 2020

Related U.S. Application Data

(63) Continuation-in-part of application No. 16/735,979, filed on Jan. 7, 2020, now Pat. No. 10,722,638.

(51) Int. Cl.
*A61M 25/00* (2006.01)
*A61M 25/10* (2013.01)
*A61B 90/00* (2016.01)

(52) U.S. Cl.
CPC .......... *A61M 25/104* (2013.01); *A61B 90/37* (2016.02); *A61M 25/1011* (2013.01); *A61B 2090/3762* (2016.02); *A61M 2025/1013* (2013.01); *A61M 2025/1095* (2013.01); *A61M 2210/1082* (2013.01); *A61M 2210/125* (2013.01)

(58) Field of Classification Search
CPC ...... A61B 6/481; A61L 29/16; A61M 1/3613; A61M 1/3616; A61M 25/1011; A61M 2025/1013; A61M 2210/1082
See application file for complete search history.

(56) References Cited

U.S. PATENT DOCUMENTS

| | | |
|---|---|---|
| 6,287,273 B1 | 9/2001 | Allers et al. |
| 6,554,819 B2 | 4/2003 | Reich |
| 6,592,567 B1 | 7/2003 | Levin et al. |
| 6,699,231 B1 | 3/2004 | Sterman et al. |
| 7,363,072 B2 | 4/2008 | Movahed |
| 7,824,357 B2 | 11/2010 | Al-Rashdan |
| 8,216,209 B2 | 7/2012 | Consigny et al. |
| 8,251,942 B1 | 8/2012 | Al-Rashdan |
| 8,398,576 B2 | 3/2013 | Angheloiu |
| 8,795,219 B1 | 8/2014 | Al-Rashdan |
| 9,211,372 B2 | 12/2015 | Kaye |
| 9,308,310 B2 | 4/2016 | Hochareon |
| 9,421,330 B2 | 8/2016 | Kalafut et al. |
| 10,722,638 B1 * | 7/2020 | Wool ............... A61M 25/1011 |
| 2004/0167415 A1 | 8/2004 | Gelfand et al. |
| 2005/0256441 A1 | 11/2005 | Lotan et al. |
| 2006/0271111 A1 | 11/2006 | Demarais et al. |
| 2009/0099516 A1 | 4/2009 | Gildoni et al. |
| 2016/0030714 A1 | 2/2016 | Power et al. |
| 2019/0223935 A1 | 7/2019 | Melder |

FOREIGN PATENT DOCUMENTS

JP  2006043351 A  2/2006

* cited by examiner

*Primary Examiner* — Benjamin J Klein
(74) *Attorney, Agent, or Firm* — Bush Intellectual Property Law; Kenneth M. Bush

(57) ABSTRACT

The invention relates to a method to prevent contrast-induced nephropathy during an imaging procedure. The method includes the step of positioning balloon catheters in a patient's renal arteries and inflating the balloons of each catheter to block the flow of contrast media into the patient's kidneys.

8 Claims, 5 Drawing Sheets

METHOD FOR PREVENTING CONTRAST INDUCED NEPHROPATHY

CROSS-REFERENCE TO RELATED APPLICATIONS

The present application is a continuation-in-part (CIP) of U.S. patent application Ser. No. 16/735,979, filed Jan. 7, 2020. The present application claims priority to and benefit of U.S. patent application Ser. No. 16/735,979, which is hereby incorporated by reference in its entirety herein.

FIELD OF THE INVENTION

The present invention relates to contrast-induced nephropathy (CIN) and to methods for reducing and/or preventing CIN during cardiac catheterization, percutaneous transluminal coronary angioplasty (PTCA), or other procedures requiring iodinated contrast such as CT scans.

BACKGROUND OF THE INVENTION

Contrast angiography provides an effective means for imaging arteries and organs during diagnostic and interventional medical procedures. The majority of such procedures are cardiac related. For example, cardiac catheterization and percutaneous transluminal coronary angioplasty (PTCA) both rely on the presence of contrast media in cardiac vessels to enable imaging during diagnostic and/or treatment procedures. Cardiac catheterization and PTCA procedures are frequently performed by inserting a catheter into the femoral artery and guiding the catheter to the ostium of a coronary artery where contrast dye is injected and cineangiography images are obtained. If severe stenosis is present, PTCA can be performed with a balloon catheter to open a blocked vessel and/or to implant one or more stents.

During an imaging procedure, iodinated contrast media is injected into a blood vessel of a patient. The contrast media causes an attenuation in an X-ray or CT beam used in the imaging procedure, thereby allowing a physician to visualize blood vessels and organs that contain the contrast material.

While contrast imaging has revolutionized diagnostic and therapeutic medical practice, it may induce renal impairment, a condition referred to as contrast-induced nephropathy (CIN). Contrast-induced nephropathy occurs when the kidneys are exposed to contrast media during imaging procedures resulting in transient or permanent renal impairment or even kidney failure.

Kidney dysfunction resulting from exposure to radiographic contrast media is believed to be a consequence of cytotoxic effects on renal tubular epithelial cells, and/or ischemic effects on the blood vessels of the renal medullary bed, induced by exposure to contrast media. Certain individuals appear to be more susceptible or at higher risk to CIN, for example, those having diabetes, or patients with baseline kidney disease.

Previous attempts to prevent or ameliorate CIN have included administering cytoprotective pharmaceutical agents, and methods that remove or reduce the concentration of contrast media in the blood including, for example, hemodialysis, hemofiltration, and hydration. Only hydration has been shown to be beneficial in preventing CIN.

There remains a need for improved methods to prevent contrast-induced nephropathy. The present invention provides an improved method for preventing CIN during an imaging procedure.

SUMMARY OF THE INVENTION

The present invention provides a method for preventing CIN by isolating the kidneys from exposure to contrast media during an angiographic procedure. The method can be performed during any procedure requiring contrast. Procedurally, the method is based on blocking the flow of blood from the general circulation into the kidneys thereby preventing exposure to contrast material.

In a preferred embodiment, the method relates to isolating the kidneys from the general circulation by blocking the flow of blood from the general circulation into the kidneys. Isolating the kidneys is accomplished by placing balloon catheters at the ostium of the renal artery and renal vein of each kidney. After inflating the balloons, blood flow to the kidneys is blocked thereby isolating the kidneys and preventing exposure to contrast media in the general circulation.

The kidneys are isolated from the remainder of the circulation by balloon catheters that are inflated in the renal artery and renal vein. The catheters contain a central lumen which, when connected to a pump-oxygenator, allows blood to the kidneys to be perfused in closed-loop fashion, thereby preventing exposure to contrast media.

In an alternate embodiment, the method relates to blocking the flow of blood from the general circulation into the kidneys by placing balloon catheters at the ostium of only the renal artery of each kidney. After inflating the balloons, blood flow to the kidneys is blocked thereby isolating the kidneys and preventing exposure to contrast media in the general circulation. Rather than blocking the renal veins, fluid flow from the kidneys through the renal veins to the general circulation is permitted in this embodiment. A minimal volume of perfusate is provided to the kidneys through the canula lumen from a remote source.

These and other aspects and advantages of the invention will be apparent from the following description and the appended claims. This Summary is provided merely to introduce certain concepts and is not intended to identify any key or essential features of the claimed subject matter.

DETAILED DESCRIPTION OF THE INVENTION

Figure 1:
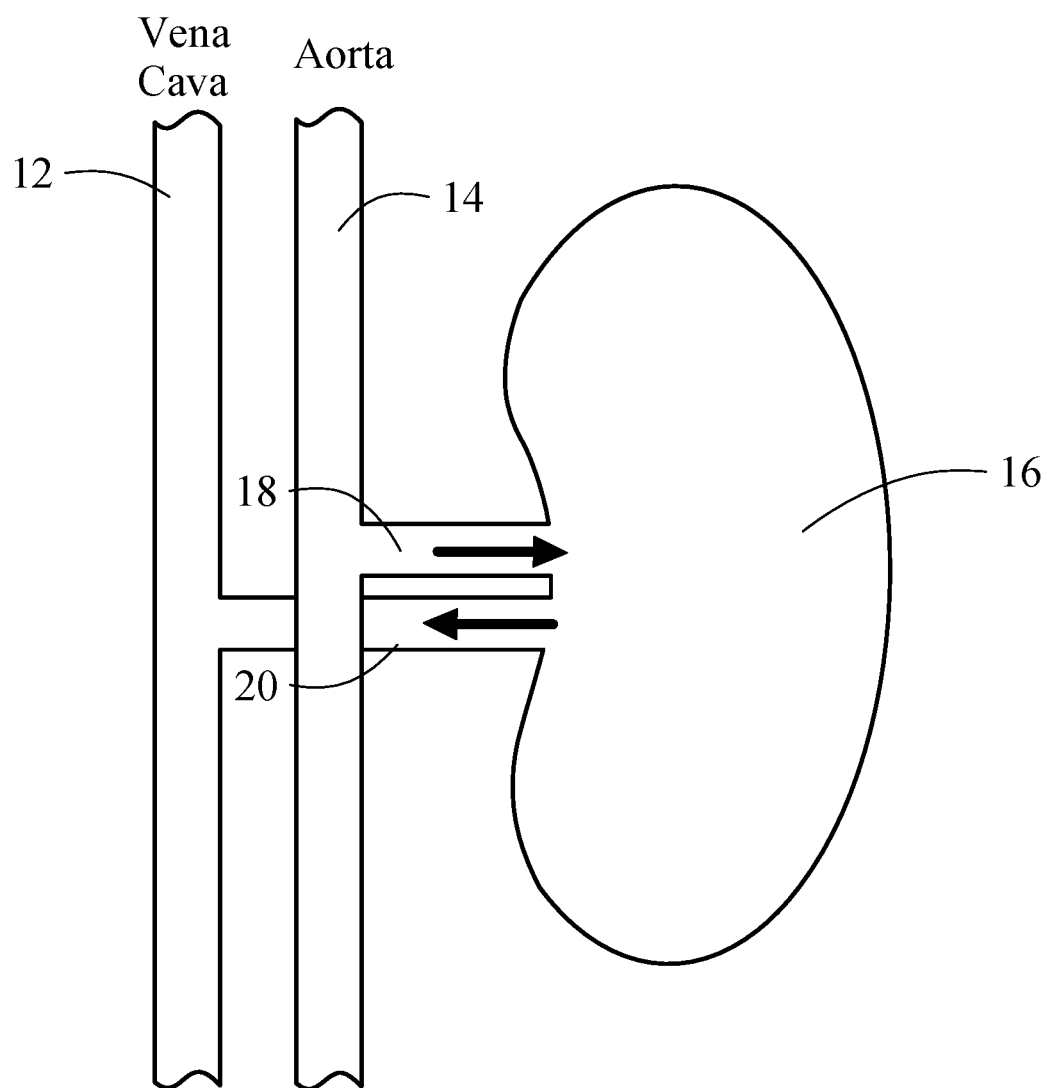
FIG. 1 schematically represents normal blood flow to and from the kidneys and the general circulation.

Contrast-induced nephropathy (CIN) can be prevented by isolating the kidneys from exposure to contrast media. The method of the invention relates to preventing exposure of the kidneys to contrast media during a cardiac catheterization or PTCA procedure. The method is performed on both kidneys, assuming both kidneys are present. For simplification, the ensuing discussion is limited to the left kidney, but it should be understood that the same procedure would be performed on the right kidney. With reference now to FIG. 1, shown schematically is a portion of the circulatory system depicting the left kidney 16, vena cava 12, aorta 14, left renal artery 18 and left renal vein 20. In the normal situation, blood flows from the aorta 14 to the renal artery 18, and from the kidneys to the renal vein 20 and vena cava 12. Without some type of intervention, contrast media enters the general circulation including the vena cava 12 and aorta 14 and eventually reaches the kidneys 16.

Figure 2:
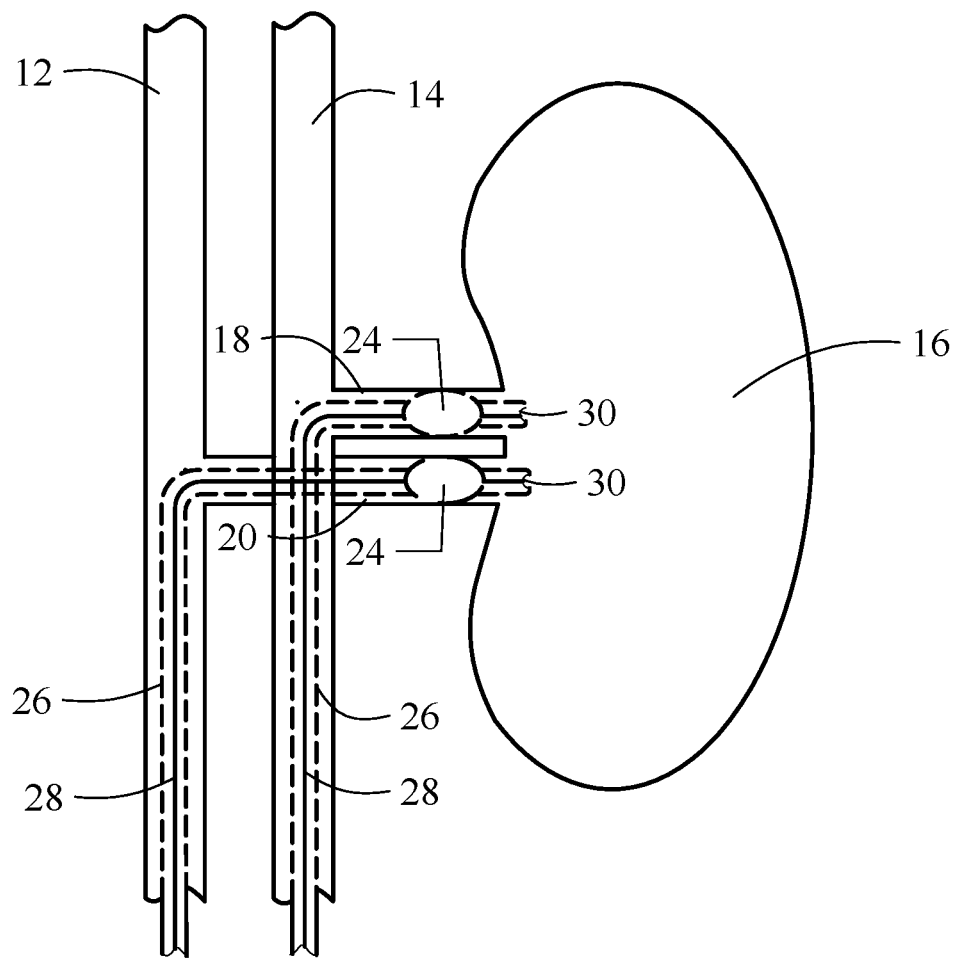
FIG. 2 shows a schematic representation of a preferred embodiment of the invention whereby blood flow to the kidneys from the general circulation, and blood flow from the kidneys to the general circulation, is blocked by placing balloon catheters in the renal artery and renal vein.

As shown in FIG. 2, the preferred embodiment of the invention provides a method for preventing exposure of the kidneys to contrast media in the general circulation during an imaging procedure. According to the method, a balloon catheter 26 is inserted into the left renal artery 18 and the left renal vein 20. Each catheter 26 includes a balloon 24 at the distal end, and a central lumen 28. Each catheter also includes a port or opening 30 located at or near the distal end that is in fluid communication with lumen 28. The proximal end of each catheter is connected to a pump-oxygenator 35 (see FIG. 3). Balloon catheters used according to the present method are of conventional design, allowing the balloons to be inflated and deflated as desired.

Catheters 26 are positioned such that balloons 24 can be inflated to completely occlude renal artery 18 and renal vein 20. This procedure isolates the kidneys from the rest of the circulation, thereby preventing exposure to contrast material.

Figure 3:
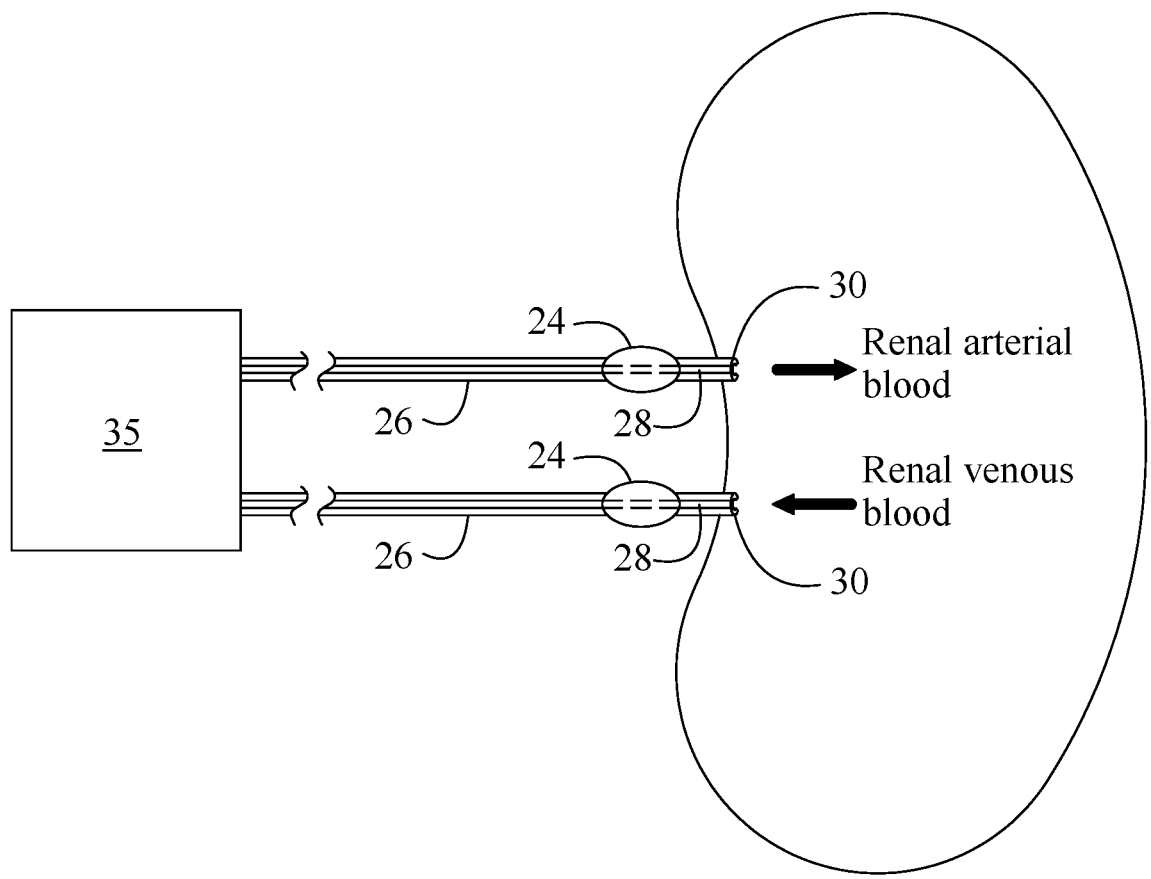
FIG. 3 provides a schematic representation of the preferred embodiment of FIG. 2 whereby intravascular renal blood is isolated from the general circulation and pumped through a pump-oxygenator.

With reference now to FIG. 3, after inflation of balloons 24, the blood in the kidneys drains into catheter lumens 28 through distal ports 30 and is circulated through a pump-oxygenator 35 located outside the body to maintain appropriate carbon dioxide and oxygen levels during the procedure, and then returned to the renal arteries.

After the imaging procedure is finished and the contrast has been cleared from the general circulation, the catheter balloons are deflated and the catheters are removed from the patient's body.

Accordingly, the preferred embodiment of the present invention is a method for preventing contrast-induced nephropathy during an imaging procedure, comprising the steps of (1) inserting a first catheter containing a first inflatable balloon at a first catheter distal end in a patient's right renal artery, (2) inserting a second catheter containing a second inflatable balloon at a second catheter distal end in the patient's left renal artery, (3) inserting a third catheter containing a third inflatable balloon at a third catheter distal end in the patient's right renal vein, (4) inserting a fourth catheter containing a fourth inflatable balloon at a fourth catheter distal end in the patient's left renal vein, (6) inflating each inflatable balloon to block the flow of blood from the patient's blood circulation to the patient's kidneys, and from the patient's kidneys to the patient's blood circulation, (7) introducing contrast media into the patient's blood circulation, (8) performing the imaging procedure, (9) deflating each inflatable balloon, and (10) removing each catheter from the patient.

Figure 4:
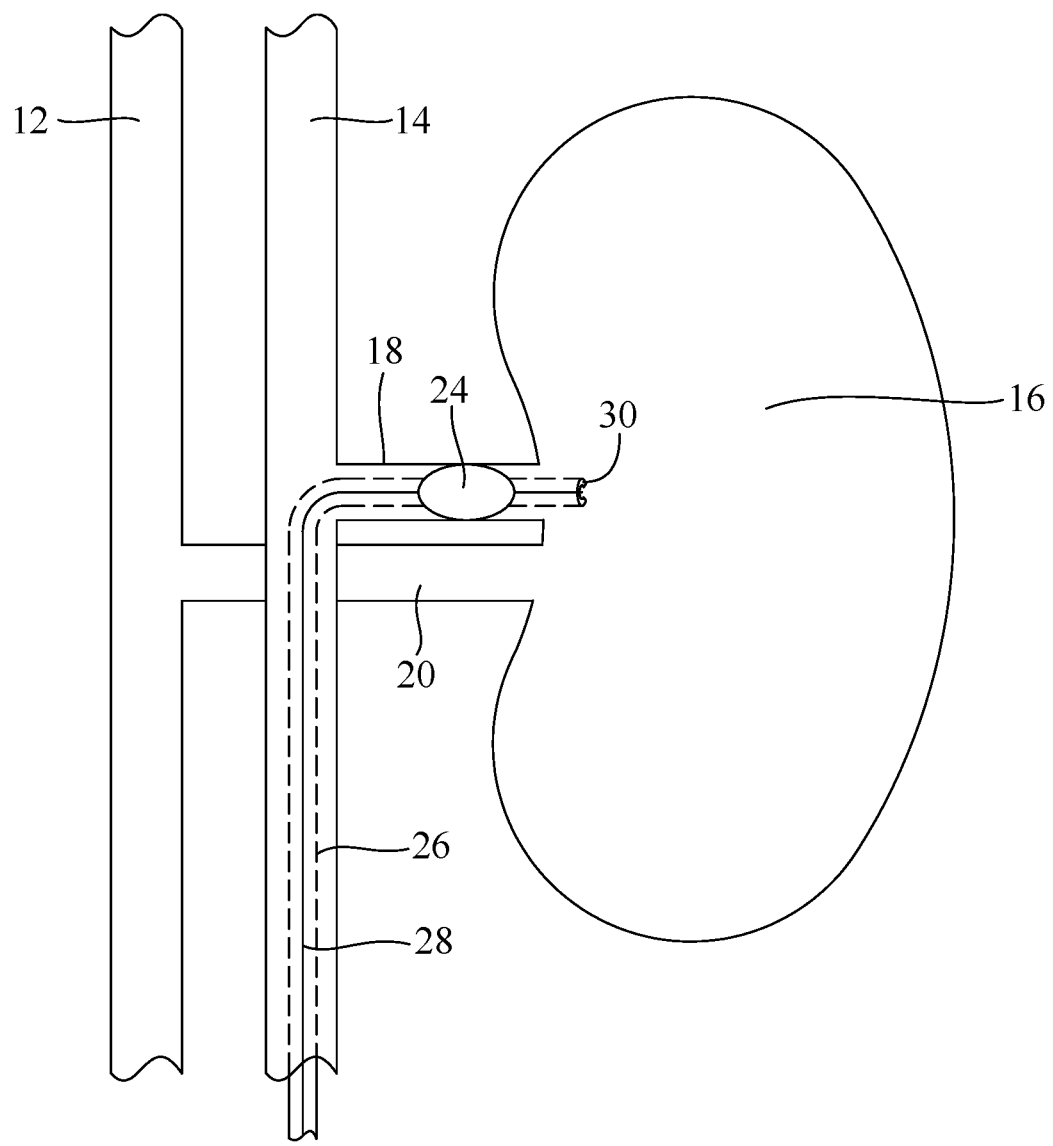
FIG. 4 shows a schematic representation of an alternate embodiment of the invention whereby blood flow to the kidneys from the general circulation is blocked by placing a balloon catheter only in the renal artery.
Figure 5:
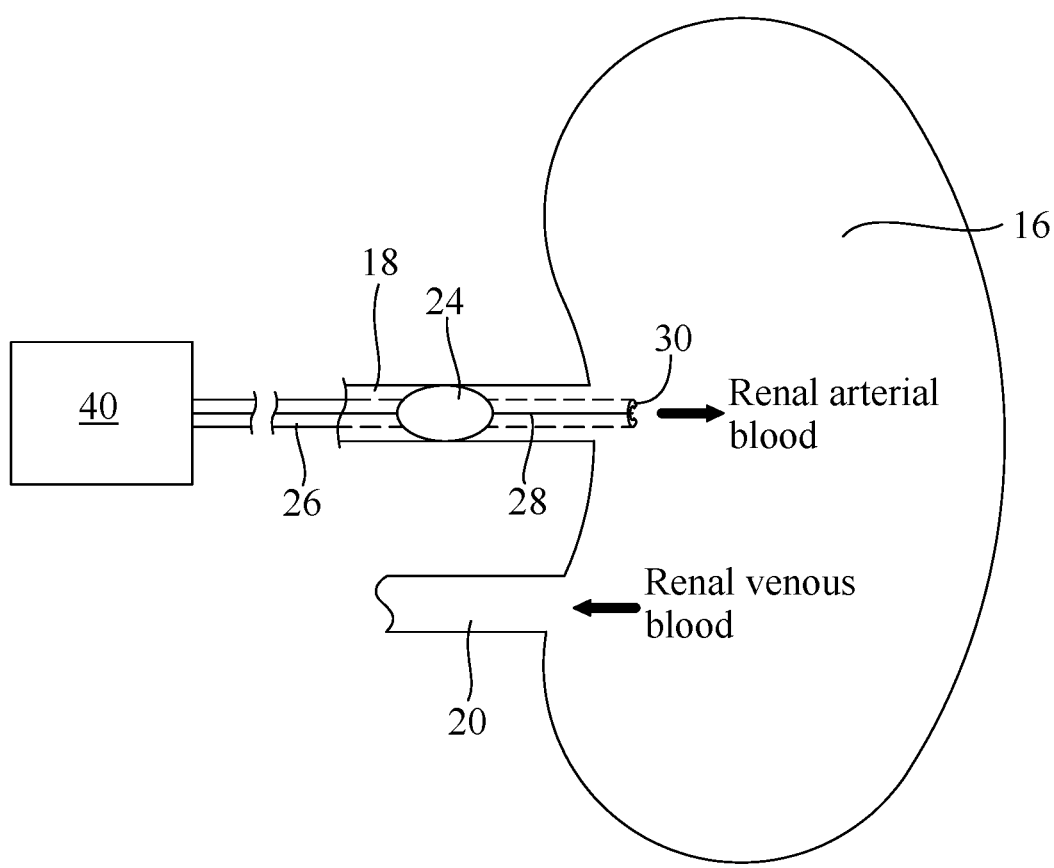
FIG. 5 provides a schematic representation of the embodiment of FIG. 4 whereby blood flow to the kidneys from the general circulation is blocked and the kidney is supplied with perfusate from a remote source.

FIGS. 4-5 illustrate an alternate embodiment of the invention whereby blood flow to the kidneys from the general circulation is blocked by placing a balloon catheter only in the renal arteries. Rather than blocking the renal veins, fluid flow from the kidneys through the renal veins to the general circulation is permitted in this embodiment. Since the kidneys will not need to perform their filtering function during the imaging procedure, a reduced flow of perfusate should be sufficient to oxygenate the kidneys to maintain their viability. The perfusate is provided through the canula lumen 28 from a remote source 40. The perfusate can be the patient's own blood (banked prior to the procedure), donor blood, or a blood substitute. By avoiding the steps of cannulating the renal veins, the overall procedure is simplified and thus the procedure time is reduced.

While the invention has been shown and described in some detail with reference to specific exemplary embodiments, there is no intention that the invention be limited to such detail. On the contrary, the invention is intended to include any alternative or equivalent embodiments that fall within the spirit and scope of the invention as described herein and as set forth in the following claims.

What is claimed is:

1. A method for preventing contrast-induced nephropathy during an imaging procedure, comprising the steps of:
   a) inserting a first catheter containing a first inflatable balloon at a first catheter distal end in a patient's right renal artery;
   b) inserting a second catheter containing a second inflatable balloon at a second catheter distal end in the patient's left renal artery;
   c) inflating each inflatable balloon to block the flow of blood from the patient's blood circulation to the patient's kidneys;
   d) introducing contrast media into the patient's blood circulation;
   e) performing the imaging procedure;
   f) deflating each inflatable balloon; and
   g) removing each catheter from the patient.

2. A method according to claim 1 wherein each catheter includes a proximal end that is operably connected to a source of perfusate.

3. A method according to claim 2 wherein each catheter further includes a central lumen that is in fluid communication with the patient's kidneys.

4. A method as in claim 1 wherein the imaging procedure is performed during a cardiac catheterization or PTCA procedure.

5. A method for preventing contrast-induced nephropathy during an imaging procedure, comprising the steps of:
   a) inserting a catheter containing an inflatable balloon at a catheter distal end in a patient's renal artery;
   b) inflating the inflatable balloon to block the flow of blood from the patient's blood circulation to the patient's kidney;
   c) introducing contrast media into the patient's blood circulation;
   d) performing the imaging procedure;
   e) deflating the inflatable balloon; and
   f) removing the catheter from the patient.

6. A method according to claim 5 wherein the catheter includes a proximal end that is operably connected to a source of perfusate.

7. A method according to claim 6 wherein the catheter further includes a central lumen that is in fluid communication with the patient's kidneys.

8. A method according to claim 5 wherein the imaging procedure is performed during a cardiac catheterization or PTCA procedure.

* * * * *